United States Patent [19]
Peeters et al.

[11] Patent Number: 5,835,975
[45] Date of Patent: Nov. 10, 1998

[54] PAPER PROPERTY SENSING SYSTEM

[75] Inventors: Eric Peeters, Mountain View, Calif.; Joel A. Kubby; Fred F. Hubble, III, both of Rochester, N.Y.; Stanley J. Wallace, Victor, N.Y.; Alan J. Werner, Jr.; R. Enrique Viturro, both of Rochester, N.Y.

[73] Assignee: Xerox Corporation, Stamford, Conn.

[21] Appl. No.: 666,765

[22] Filed: Jun. 19, 1996

[51] Int. Cl.$^6$ .................................................. G01N 19/02
[52] U.S. Cl. .................... 73/9; 338/2; 73/777; 73/862.55
[58] Field of Search ........................ 73/862.041, 862.55, 73/862.637, 9, 10, 777, 841, 842, 843, 844, 862.046; 338/2

[56] References Cited

U.S. PATENT DOCUMENTS

| | | | |
|---|---|---|---|
| 3,123,788 | 3/1964 | Pfann et al. | 73/777 |
| 3,145,563 | 8/1964 | Hollander, Jr. | 73/777 |
| 3,266,303 | 8/1966 | Pfann | 73/777 |
| 3,270,554 | 9/1966 | Pfann | 73/777 |
| 4,016,756 | 4/1977 | Kunkle | 73/862.041 |
| 4,141,253 | 2/1979 | Whitehead, Jr. | 73/727 |
| 4,224,513 | 9/1980 | Casey et al. | 250/216 |
| 4,277,177 | 7/1981 | Larsen et al. | 356/431 |
| 4,442,717 | 4/1984 | Kurtz et al. | 73/862.623 |
| 4,493,548 | 1/1985 | Ateya | 355/3 FU |
| 4,528,507 | 7/1985 | Domin et al. | 324/229 |
| 4,610,530 | 9/1986 | Lehmbeck et al. | 355/14 TR |
| 4,641,949 | 2/1987 | Wallace et al. | 355/3 SH |
| 4,966,455 | 10/1990 | Avni et al. | 356/73 |
| 5,109,236 | 4/1992 | Watanabe et al. | 346/76 PH |
| 5,276,327 | 1/1994 | Bossen et al. | 250/339 |
| 5,389,795 | 2/1995 | Rye | 250/572 |
| 5,490,089 | 2/1996 | Smith et al. | 364/514 R |
| 5,503,029 | 4/1996 | Tamori | 73/862.041 |
| 5,526,701 | 6/1996 | Tamori | 73/862.041 |

OTHER PUBLICATIONS

Process development for 3D silicon microstructures, with applic. to mech. sensors, by E. Peeters, Katholieke Universiteit Leuven, Mar. 1994, pp. 150–159, 279–300.

Bryzek, J. et al., Micromachines on the March. IEEE Spectrum, May 1994, pp. 20–31.

Konishi, S. et al., A Conveyance System Using Air Flow Based on the Concept of Distributed Micro Motion Systems. Journal of Microelectromechanical Systems, vol. 3, No. 2, Jun. 1994, pp. 54–58.

Konishi, S. et al., System Design for Cooperative Control of Arrayed Microactuators. Proceedings of the IEEE Micro Electro Mechanical Systems 1995, IEEE, Piscataway, NJ, USA 95CH35754, pp. 322–327.

Paivanas, J.A. et al., Air Film System for Handling Semiconductor Wafers. IBM J. Res. Develop., vol. 23, No. 4, Jul. 1979, pp. 361–375.

Terry, S. et al., Silicon Pressure Transducer Arrays for Blood–Pressure Measurement. Sensors and Actuators, 1990, pp. 1070–1079.

*Primary Examiner*—Ronald L. Biegel
*Attorney, Agent, or Firm*—Tracy L. Hurt

[57] ABSTRACT

A sensor system for measuring physical properties of paper. The paper property sensor system includes a surface and a diaphragm opposed to each other. The small diaphragm includes a first pair and a second pair p-type piezoresistors. Each piezoresistor of the first pair has a longitudinal axis and is located perpendicular to and very close to one of the long edges of the diaphragm. Each piezoresistor of the second pair has a longitudinal axis and is located between and parallel to first pair of piezoresistors, and away from the short edges of the diaphragm. Coupling the first pair of piezoresistors with the second pair via a Wheatstone bridge produces a voltage representative of the shear force exerted by a sheet.

23 Claims, 11 Drawing Sheets

PAPER PROPERTY SENSING SYSTEM

FIELD OF THE INVENTION

The present invention relates to sensor systems for sheet handling devices. In particular, the present invention relates to a sensor system for determining the coefficient of friction and thickness of paper.

BACKGROUND OF THE INVENTION

A. Reproductive Machines

The quality of text or images written to or read from a markable medium such as paper by devices such as laser printers, xerographic printers, scanners, or ink jet printers is highly dependent on physical characteristics of the medium. The thickness, curl, mass, and stiffness of the medium being marked all affect the speed and accuracy with which a printer can transport a sheet of a the medium, as well as affecting the accuracy with which text or images can be transferred to the medium. Generally, printers and copiers work well only with a limited range of paper types, with a sheet transport mechanism and an image transfer mechanism optimized for that range. In extreme cases, reasonable print quality is only possible with specially developed paper supplied by the manufacturer and maintained in pristine condition, unbent and at certain humidity levels to limit curling. A sheet that is too thick, too thin, or even slightly curled may increase the risk jamming or blocking the sheet transport mechanism.

One solution might be to provide various sheet type settings for printers, copiers, and scanners to prevent errors in sheet transport, and increase image quality without necessarily requiring specific manufacturer supplied papers. For example, a user could manually select a "thick paper" setting if thicker papers or thin cardboard stock is to be fed through the sheet transport mechanism. Spacing of pinch rollers and speed of transport would then be automatically adjusted to compensate for the increased paper thickness. Unfortunately, this solution requires extra effort from a user to identify the correct grade or type of markable medium being supplied to the printer. Further, this system is somewhat unwieldy if multiple paper types are intermixed, since the "thick paper" setting must be regularly enabled and disabled by the user as various paper types are fed through the sheet transport mechanism.

Thus, a need exists for an inexpensive sheet handling system that automatically detects sheet properties, and automatically adjusts settings of a sheet transport mechanism to optimize sheet handling speed, spacing, or other paper transport characteristics based on the detected paper properties. Such a system would require minimal input from a user, and would automatically attempt to optimize its sheet handling characteristics to support use of a wide range of markable mediums. Such a sheet handling system would allow for greater use of recyclable papers of differing quality and consistency, and could limit paper wastage by permitting use of lower quality or even slightly damaged papers, while still providing transport results comparable to those of pristine, newly manufactured papers.

Additionally, a need exists for a sheet handling system that provides information concerning sheet properties to allow for optimizing adjustments in an image transfer mechanism. If sheet properties such as heat capacity, thermal conductivity, dielectric constants, or resistance are determined prior to image transfer, the image transfer mechanism can be suitably optimized to ensure the best possible text or image transfer.

B. Silicon Pressure Transducers

The drive toward miniaturization led to the development of silicon pressure transducers. FIG. 1 illustrates one typical prior silicon pressure transducer 100. Transducer 100 is a square silicon (100) diaphragm 102 aligned with the <110> crystal orientation, 1 mm square. Diaphragm 102 includes four piezoresistors 124 and 126, 128, and 130. Piezoresistors 124 and 128 are located perpendicular to their associated edges 104 and 108 and so close to their associated edges as to be in the region of maximum compressive stress. Piezoresistors 124 and 128 are stressed longitudinally when force is applied to diaphragm 102. In contrast, piezoresistors 126 and 130 are parallel to their associated edges and are located so close to their associated edges 106 and 110 as to be in the region of maximum compressive stress. Piezoresistors 126 and 130 are stressed transversely to their longitudinal axes when force is applied to diaphragm 102. These piezoresistors are coupled together in a Wheatstone bridge so that the longitudinal stress ($+\Delta R$) of piezoresistors 124 and 128 balances the transversal stress ($-\Delta R$) of piezoresistors 126 and 130. The output voltage of the Wheatstone bridge is proportional to the pressure applied to diaphragm 102.

FIG. 2A illustrates contours of constant deflection over a quarter of diaphragm 102 when uniformly pressurized. FIG. 2B illustrates contours of constant y-component of stress for a quarter of diaphragm 102 when uniformly pressurized. FIG. 3 is a dark field optical micrograph of diaphragm 102 when uniformly pressurized.

SUMMARY OF THE INVENTION

An object of the present invention is to enable automatic adjustment of sheet handling in response to physical properties of a sheet of a markable medium.

Another object of the present invention is to enable optimization of sheet transport mechanisms to permit use of a wide range of markable media.

A still further object of the present invention is to reduce jams in sheet transport mechanisms.

These and other objects are satisfied by a paper property sensor system including a surface and a diaphragm opposed to each other and in contact with a sheet of a markable medium. The small, rectangular diaphragm includes a first pair and a second pair piezoresistors. Each piezoresistor of the first pair has a longitudinal axis and is located perpendicular to and adjacent to one of the long edges of the diaphragm. Each piezoresistor of the second pair has a longitudinal axis that is located between and parallel to first pair of piezoresistors, and away from the short edges of the diaphragm. Coupling the first pair of piezoresistors with the second pair in a Wheatstone bridge, produces a voltage representative of the shear force exerted by the sheet.

Other objects, features, and advantages of the present invention will be apparent from the accompanying drawings and detailed description that follows.

BRIEF DESCRIPTION OF THE DRAWINGS

The present invention is illustrated by way of example and not by way of limitation in the figures of the accompanying drawings. In the accompanying drawings similar references indicate similar elements.

DETAILED DESCRIPTION OF THE PREFERRED EMBODIMENTS

Figure 1:
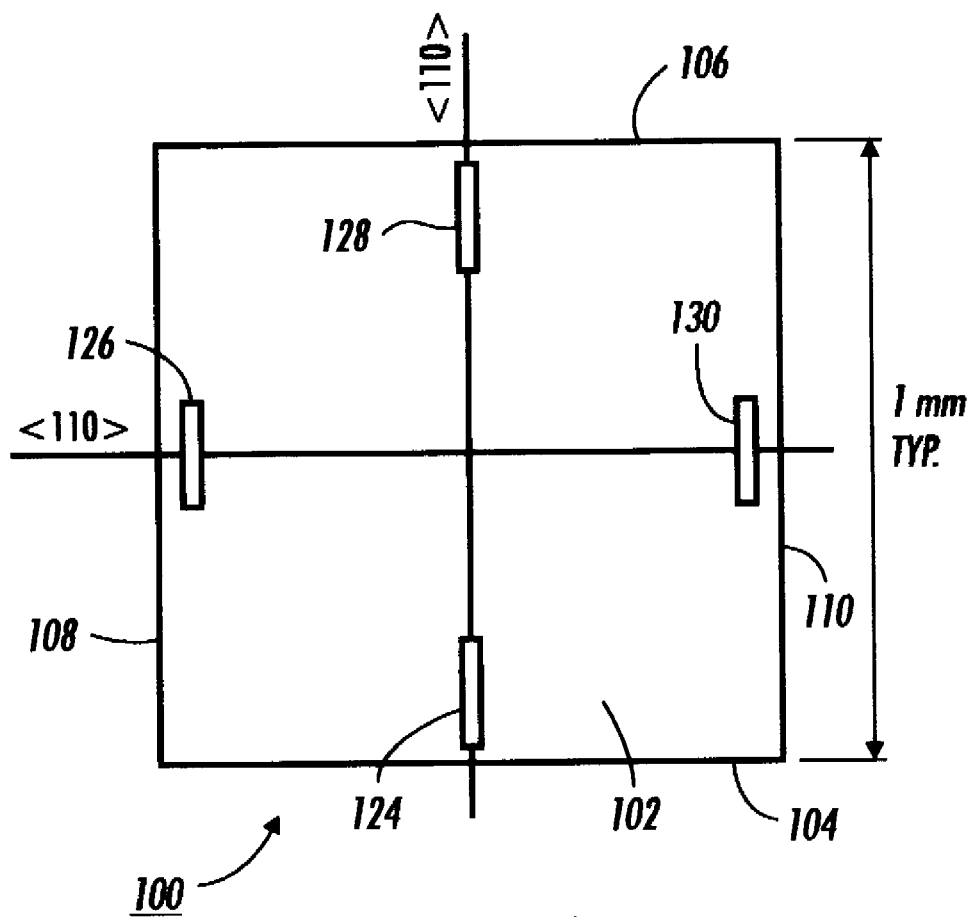
FIG. 1 illustrates a prior silicon pressure transducer.
Figure 2A:
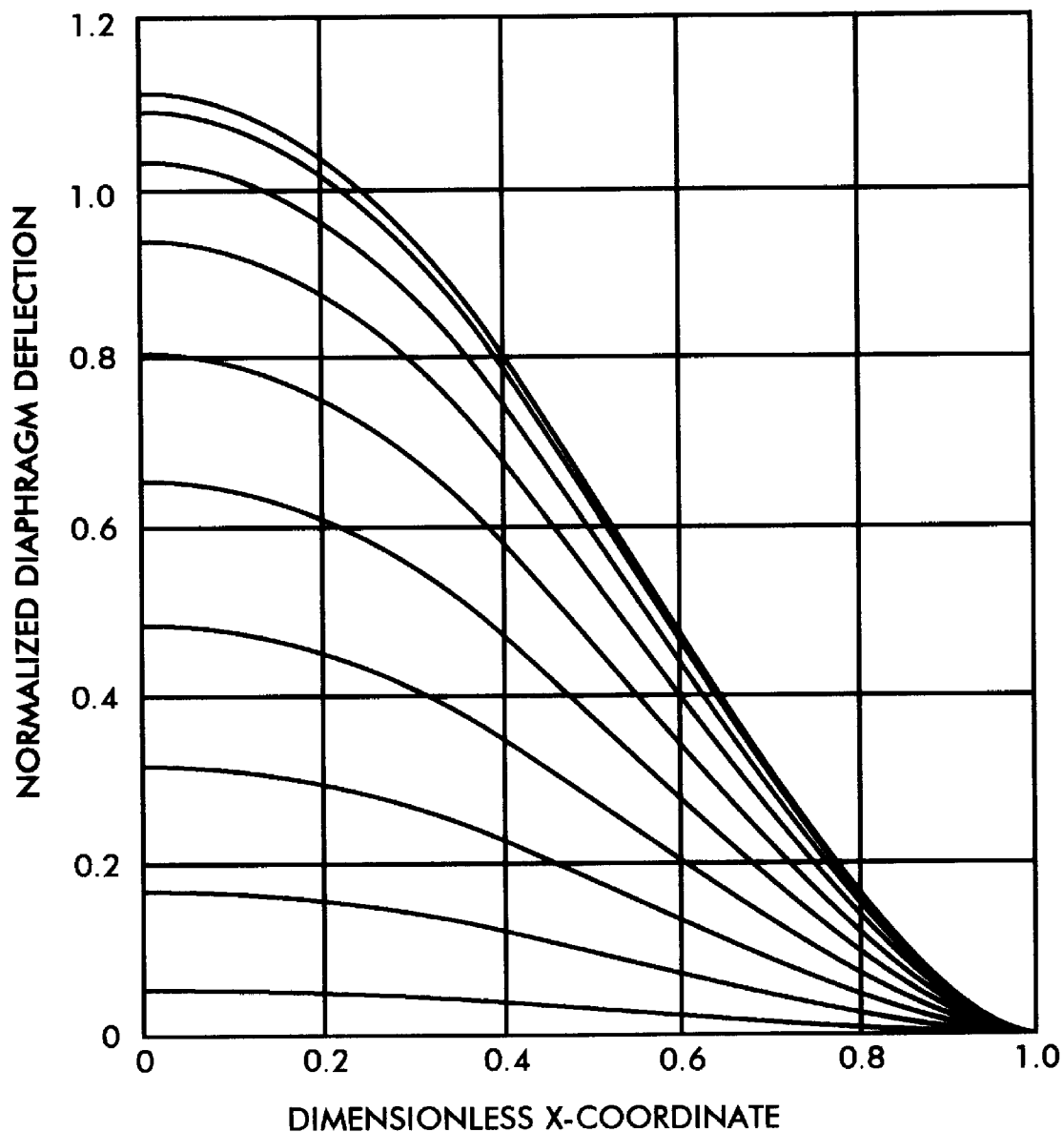
FIGS. 2A and 2B illustrate contours of constant deflection for the prior pressure transducer.
Figure 2B:
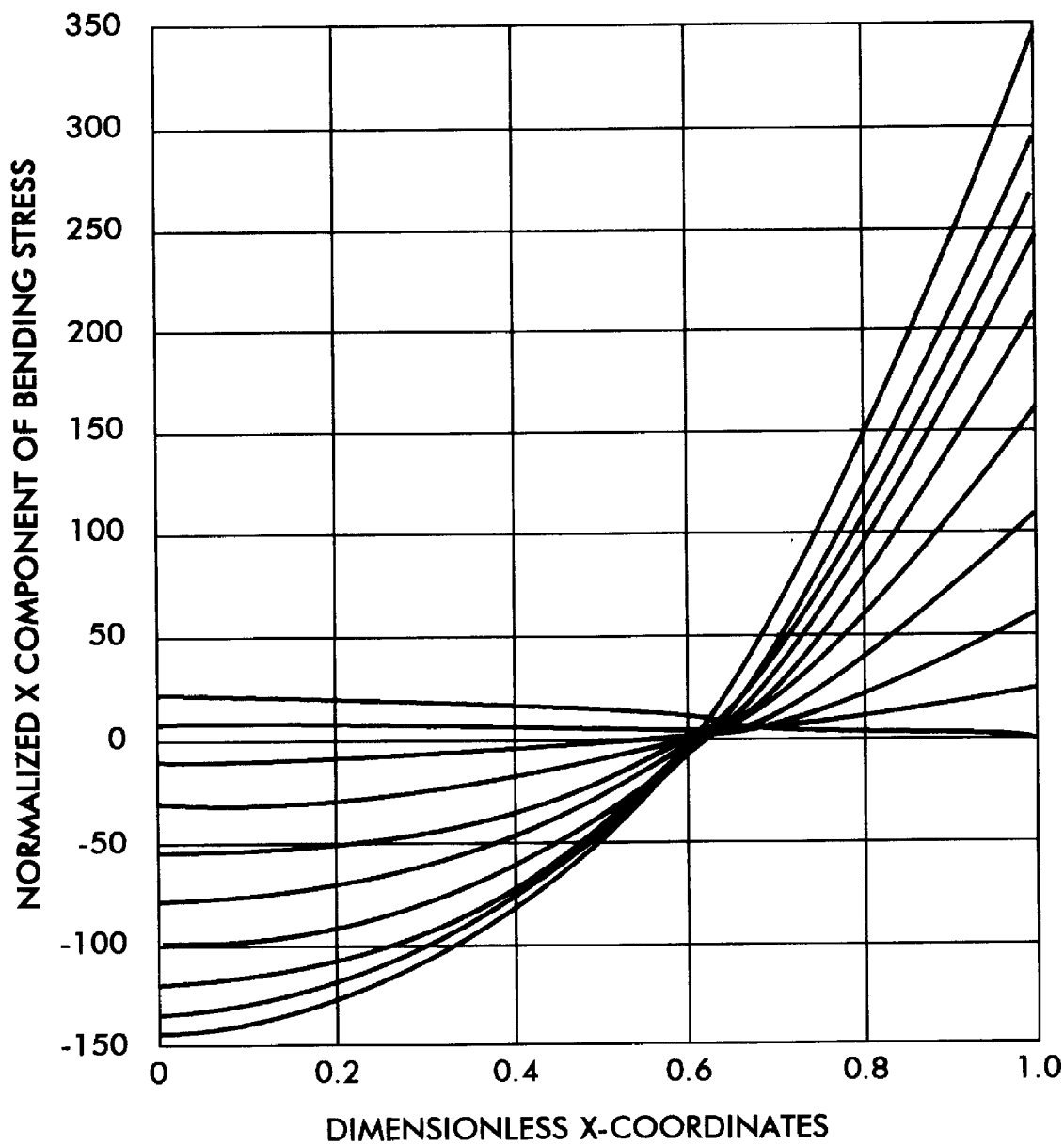
Figure 3:
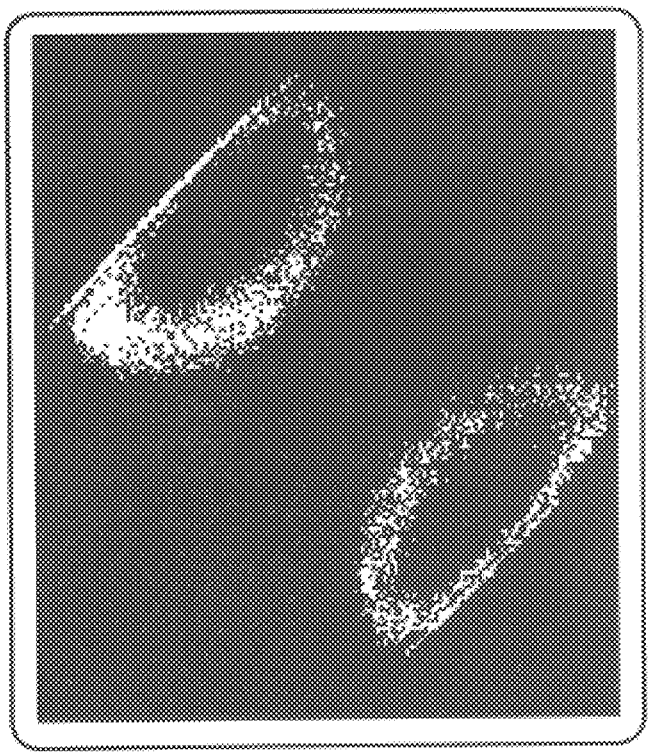
FIG. 3 is a dark field micrograph for the prior pressure transducer.
Figure 4:
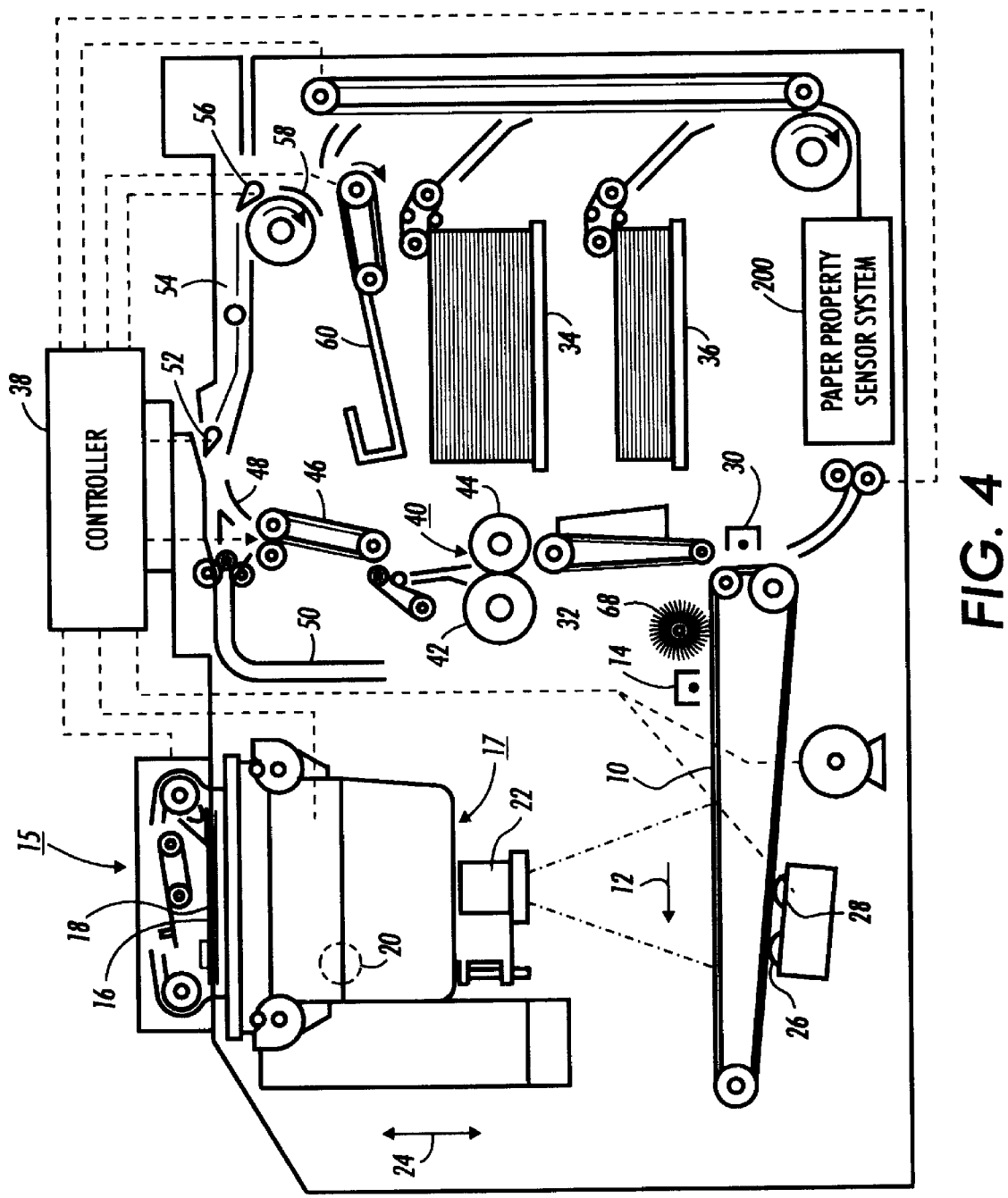
FIG. 4 illustrates a reproductive machine incorporating the paper property sensor system of the present invention.

FIG. 4 illustrates a reproductive machine 9 incorporating paper property sensor system 200 of the present invention. Paper property sensor system 200 enables reproductive machine 9 to alter its handling of sheets in response to the thickness and coefficient of friction of the sheet currently within machine 9. Briefly described, each embodiment of paper property sensor system 200 includes a surface and a diaphragm opposed to each other and in contact with the sheet of paper. The small, rectangular diaphragm includes a first pair and a second pair of piezoresistors. Each piezoresistor of the first pair is located perpendicular to and very close to one of the long edges of the diaphragm. Each piezoresistor of the second pair is located between and parallel to first pair of piezoresistors, and away from the short edges of the diaphragm. Balancing the first pair of piezoresistors against the second pair in a Wheatstone bridge, produces a voltage dependent on the thickness of a sheet. Balancing the resistors of the first pair against each other, and the resistors of the second pair against each other generates a voltage dependent on the coefficient of friction of the sheet.

Use of paper property system 200 is not limited to reproductive machine 9; system 200 can be used as part of any machine with a sheet transport mechanism.

A. The Reproductive Machine

Prior to a more detailed discussion of the paper property sensor system 200 of the present invention, consider reproductive device 9, illustrated in FIG. 4. Reproductive machine 9 includes a belt 10 having a photoconductive surface. Belt 10 moves in the direction of arrow 12 to advance successive portions of the photoconductive surface through various processing stations, starting with a charging station. The charging station includes corona generating device 14, which charges the photoconductive surface to a relatively high, substantially uniform, potential.

From the charging station, the photoconductive surface is advanced through an imaging station. At the imaging station, document handling unit 15 positions original document 16 face down over exposure system 17. Exposure system 17 includes lamp 20, which illuminates document 16 on transparent platen 18. The light rays reflected from document 16 are transmitted through lens 22, focusing the light onto the charged portion of belt 10 to selectively dissipate the charge. This records an electrostatic latent image onto the photoconductive surface of document 16.

Platen 18 is mounted movably and moves in the directions of arrows 24 to adjust the magnification of the original document being reproduced. Lens 22 moves synchronously with platen 18 to focus the light image of document 16 onto the charged portion of belt 10.

Document handling unit 15 sequentially feeds documents from a holding tray, in seriatim, to platen 18. Document handling unit 15 recirculates paper back to the stack supported on the tray. Thereafter, belt 10 advances to the electrostatic latent image to a development station.

At the development station a pair of magnetic brush developer rollers 26 and 28 advance a developer into contact with the electrostatic latent image on belt 10. The latent image attracts toner particles from the carrier granules of the developer to from a toner powder image on belt 10.

After development of the electrostatic latent image, belt 10 advances to the transfer station. At the transfer station a copy sheet is moved into contact with the toner powder image. The transfer station includes generating device 30, which sprays ions onto the backside of the copy sheet. This attracts the toner powder image from the photoconductive surface of belt 10 to the copy sheet.

The copy sheet is fed from either tray 34 or 36 to the transfer station. After transfer, conveyor 32 advances the sheet to a fusing station. The fusing station includes a fuser assembly for permanently affixing the transferred powder image to the copy sheet. Preferably, the fuser assembly includes a heated fuser roller 42 and a backup roller 44.

Paper property sensor system 200 is disposed between copy paper trays 34 and 36 and conveyor 32 at any convenient location within the copy paper transport path. Information provided by paper property sensor system 200 allows controller 38 to prevent jams by adjusting the speed of conveyors 32, 37 and 46, and the spacing between nips 39 and 41, and between rollers 42 and 44.

Controller 38 includes a processor and memory. The processor controls and coordinates the operations of reproductive machine 9 by executing instructions stored electronically in memory, including instructions for controlling paper property sensor system 200. Instructions representing the methods discussed herein may be realized in any appropriate machine language. Semiconductor logic devices that can be used to realize memory include read only memories (ROM), random access memories (RAM), dynamic random access memories (DRAM), programmable read only memories (PROM), erasable programmable read only memories (EPROM), and electrically erasable programmable read only memories (EEPROM), such as flash memories.

B. The Tactile Sensor

Figure 5:
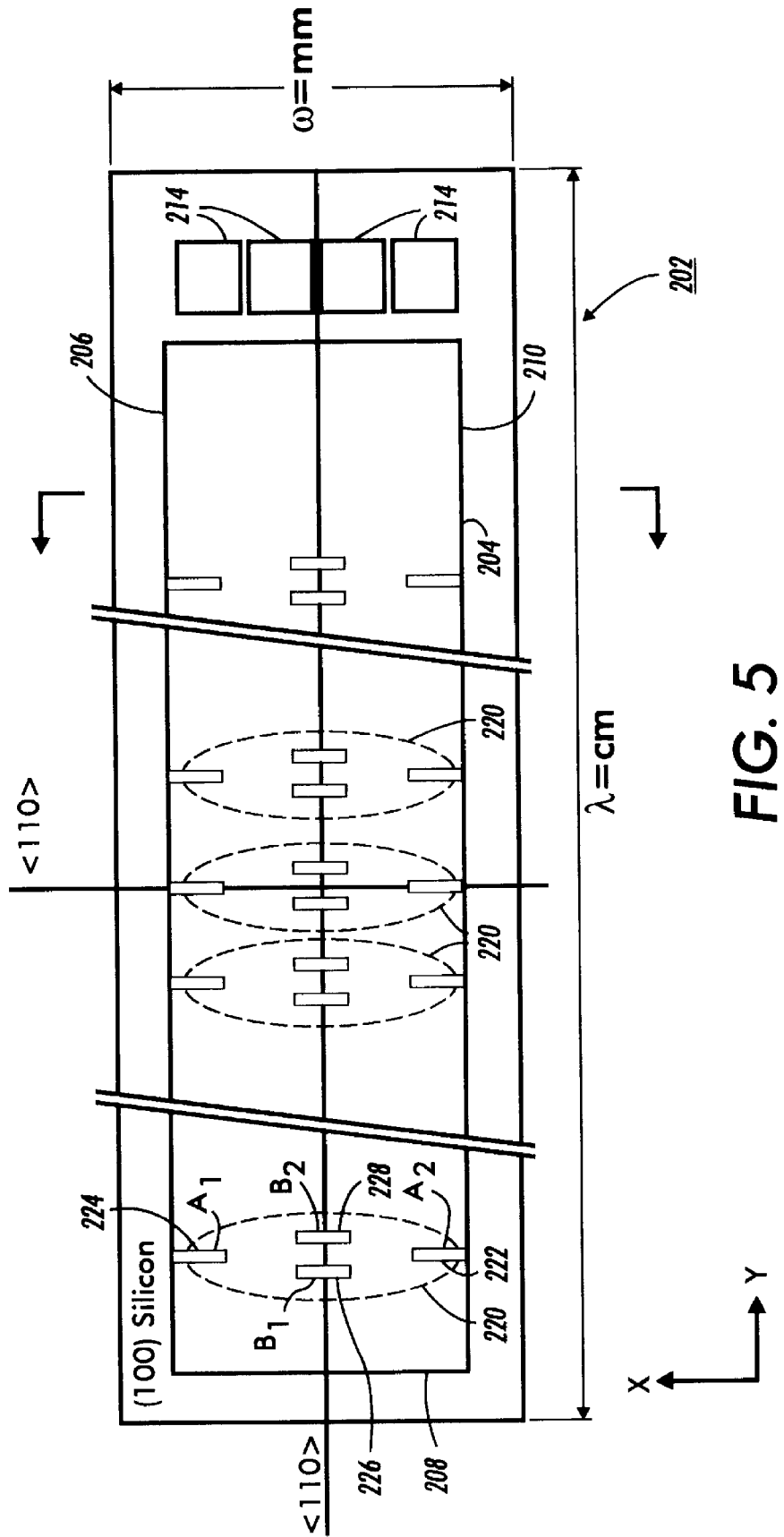
FIG. 5 illustrates a tactile sensor of the present invention.

Paper property sensor system 200 includes at least one tactile sensor 202, enabling system 200 to measure both the thickness and coefficient of friction of any sheet of material in contact with and moving past tactile sensor 202. FIG. 5 is a plan view of one tactile sensor 202. Tactile sensor 202 is a rectangular silicon (100) diaphragm aligned with the <110> crystal orientations, into which several pairs of piezoresistors have been diffused. Preferably, diaphragm 202 is n-type silicon while both pairs of piezoresistors are p-type. Parallel, opposed sides 204 and 206 range between 1–2 cm in length, while parallel, opposed sides 208 and 210 range between 1–3 mm in length. Other dimensions are possible; however, the aspect ratio should be greater than 1; i.e., diaphragm 202 should not be square for performance reasons. The depth of silicon diaphragm 202 is small compared to its width, preferably, less than a tenth of the width. Diaphragm 202 is clamped along edges 204, 206, 208, and 210, above a cavity not illustrated in this figure.

Diaphragm 202 includes several taxels 220, each of which includes two pairs of piezoresistors. Piezoresistors 222 and 224, also designated A2 and A1, form one pair, and piezoresistors 226 and 228, also designated B1 and B2, form another pair. Both piezoresistors 222 and 224 are located perpendicular to their associated edges 204 and 206. Piezoresistors 222 and 224 reside so close to their associated edges that they experience the highest compressive stress ($-\Delta R$). When pressure is applied to diaphragm 202, piezoresistors 222 and 224 experience force primarily along their longitudinal axes. Piezoresistors 226 and 228 are located between and parallel to piezoresistors 222. They are also spaced apart from and parallel to each other. Piezoresistors 226 and 228 each reside at least one half the length of edge 208 away from both edges 208 and 210. As a result, piezoresistors 226 and 228 experience force primarily along their longitudinal axes when force is applied to diaphragm 202. Piezoresistors 226 and 228 reside within the region of maximum tensile stress ($+\Delta R$).

Figure 6A:
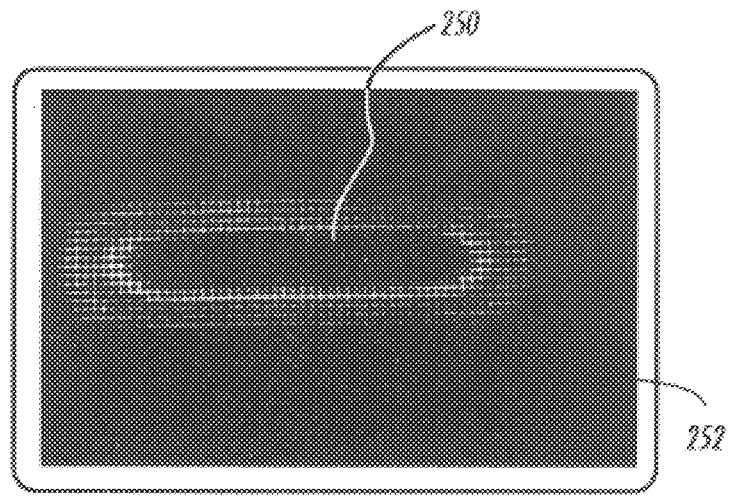
FIGS. 6A and 6B illustrate contours of constant deflection for the tactile sensor.
Figure 6B:
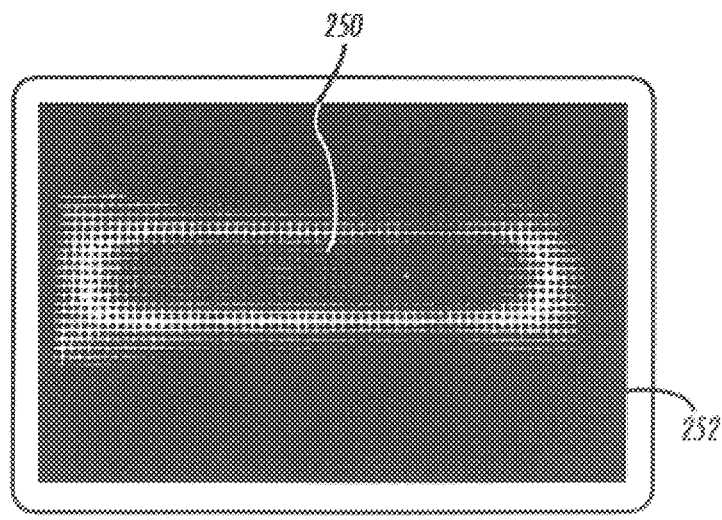

FIG. 6A illustrates contours of constant z-deflection for diaphragm 202. FIG. 6B illustrates contours of constant y-component of stress for diaphragm 202. Within FIG. 6B center black region 250 indicates the area of highest tensile stress within diaphragm 202. Piezoresistors B1 and B2 reside here. Outer black region 252 of FIG. 6B indicates the areas of highest compressive stress within diaphragm 202; this is where piezoresistors A1 and A2 reside.

Figure 7A:
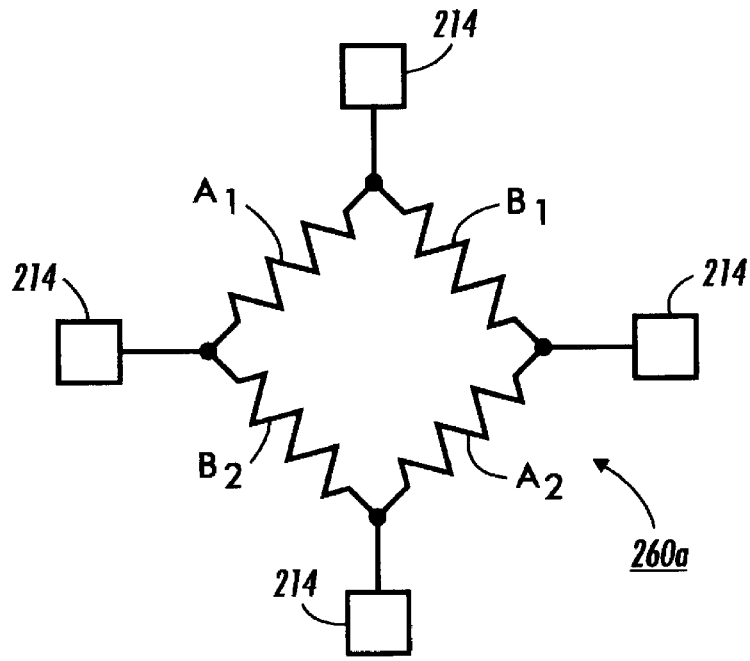
FIG. 7A illustrates a Wheatstone Bridge configuration for measuring normal force exerted on a taxel.
Figure 7B:
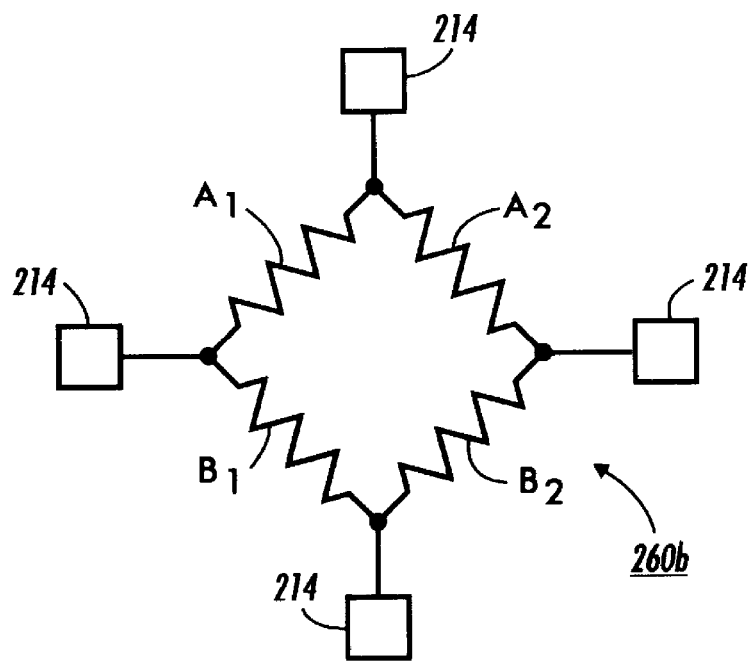
FIG. 7B illustrates a Wheatstone Bridge configuration for measuring shear force exerted on a taxel.

FIG. 7A illustrates Wheatstone Bridge 260a, which generates an output voltage representative of the normal force exerted against a taxel. This normal force is proportional to the thickness of a sheet passing over diaphragm 202. FIG. 7B illustrates Wheatstone Bridge 260b, which generates an output voltage representative of the shear force exerted against a taxel. Junctions between piezoresistors in both circuits 260a and 260b are coupled to bond pads 214.

Figure 8A:
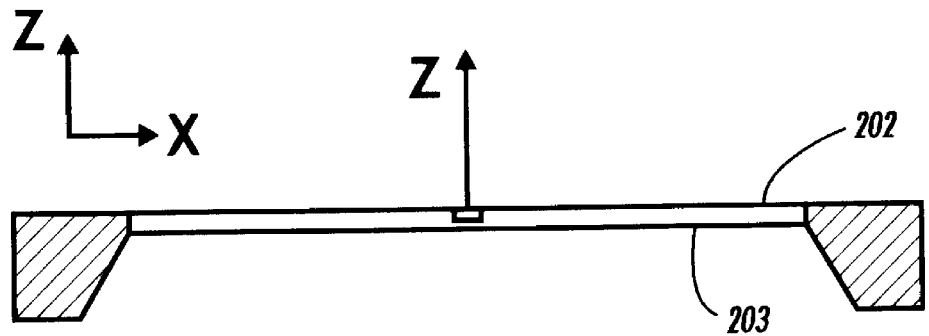
FIGS. 8A, 8B, and 8C are cross-sectional views of the tactile sensor.
Figure 8B:
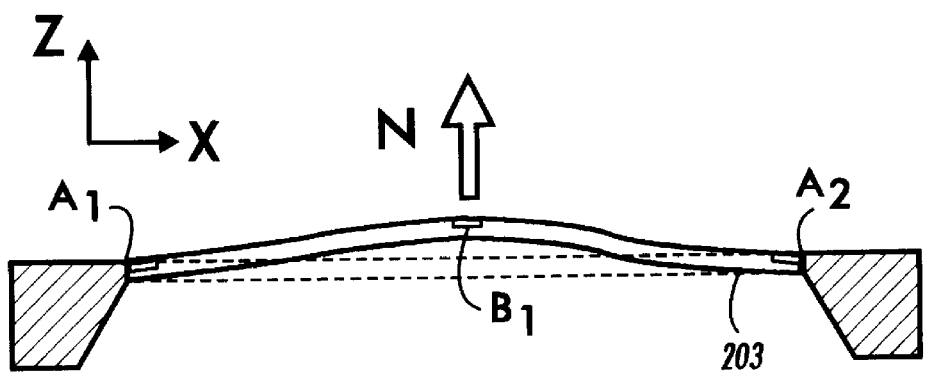
Figure 8C:
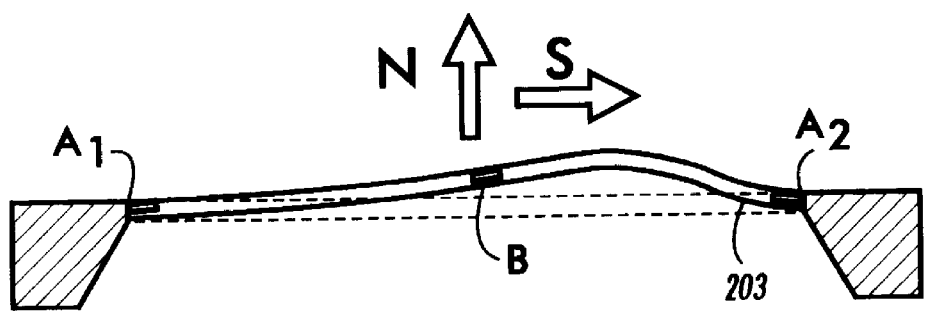

FIG. 8A is a cross-section of diaphragm 202 taken along line 216 of FIG. 5, as are FIGS. 8B and 8C. These cross-sections reveal cavity 203 underneath diaphragm 202. In the absence of pressure, diaphragm 202 is level. FIG. 8B illustrates the deformation of diaphragm 202 when subjected to a normal force, N. Normal force, N, flexes diaphragm 202 symmetrically relative to the z-axis, inducing equal stress in piezoresistors A1 and A2. Using outputs from Wheatstone bridge 260a normal force, N, is calculated according to the formula:

$$N \propto [(A1-B1)+(A2-B2)]/2.$$

Normal force, N, is a measure of the thickness of a sheet of material passing over diaphragm 202.

FIG. 8C illustrates the deformation of diaphragm 202 when subjected to both a normal force, N, and a shear force, S. Shear force, S, causes asymmetrical deformation, inducing unequal stress in piezoresistors A1 and A2. Using the outputs of Wheatstone bridge 260b, shear force, S, can be calculated according to the formula:

$$S \propto [A1-A2].$$

The ratio of shear force, S, to normal force, N, is a measure of the coefficient of friction of the sheet of material passing over diaphragm 202.

Tactile sensor 202, like many other micromachined devices, can be produced using standard semiconductor batch fabrication and wafer processing.

C. The Paper Property Sensor System

Figure 9:
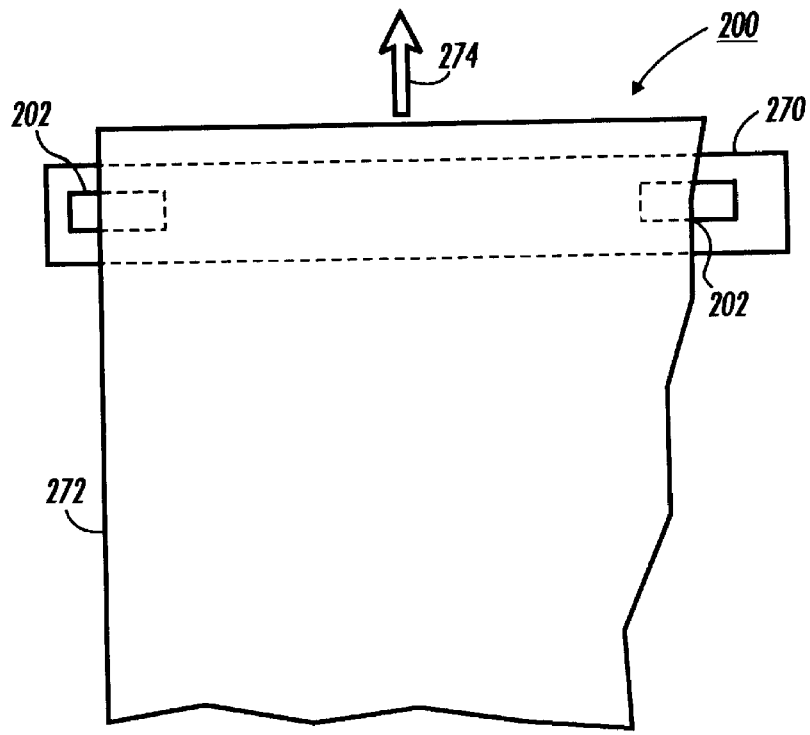
FIG. 9 is a plan view of the paper property sensor system of the present invention.

FIG. 9 is a plan view of paper property sensor 200. Paper property sensor 200 is a nip, only one surface of which is illustrated, surface 270. Both surfaces of nip 200 contact sheet of a markable medium 272 as it moves between them in the direction of arrows 274. Tactile arrays 202 of surface 270 are preferably in contact with the opposite surface when sheet 272 is not present. This approach eliminates the need for tight tolerances required in embodiments of paper property sensor system 200 with gaps between surface 270 and its opposite surface. Permanent contact between tactile array 202 and the opposite surface is achieved via an overpressure, $\Delta P$, of diaphragms 202. Constant overpressure $\Delta P$ can be achieved be sealing cavities 203 underneath diaphragms 202. Alternatively, overpressure $\Delta P$ can be modulated using a heater resistance to measure the pressure change required to keep the reaction force constant.

Figure 10:
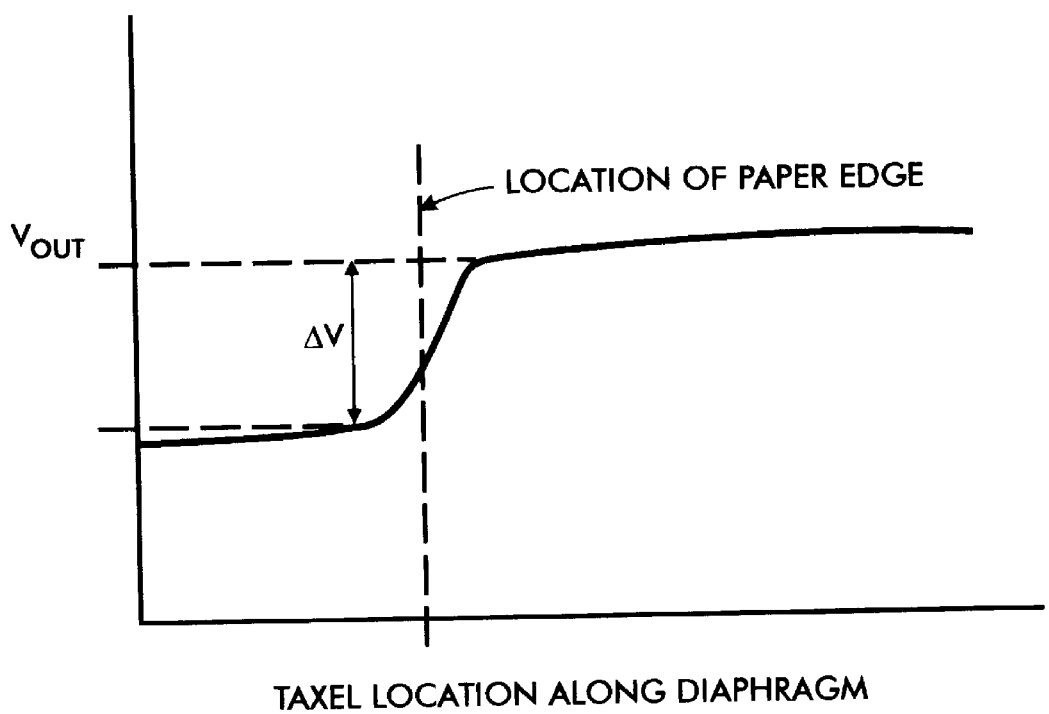
FIG. 10 is a plot of taxel output voltage versus location with the tactile array.

Tactile arrays 202 are preferably located along the longitudinal axis of surface 270 such that some of the taxels contact paper 272, and some taxels do not, as sheet 272 travels through nip 202. In combination with the constant contact, this permits differential measurements to be taken in space and in time. Differential measurements in space result from taking the output of taxels in contact with sheet 272 versus the output of taxels not in contact with paper 272. FIG. 10 graphs taxel output voltage versus taxel location. Contact with sheet 272 leads to an increase, $\Delta V$, in output voltage, which can be used to identify the edge of paper 272. Differential measurements in time result from taking the output of taxels while sheet 272 in nip 200 versus the output of taxel without sheet 272 in nip 200. Differential measurements in time and space cancel out short and long term drift in the response of tactile arrays 202 to pressure, which may result from temperature changes and wearing of surface 270.

Figure 11:
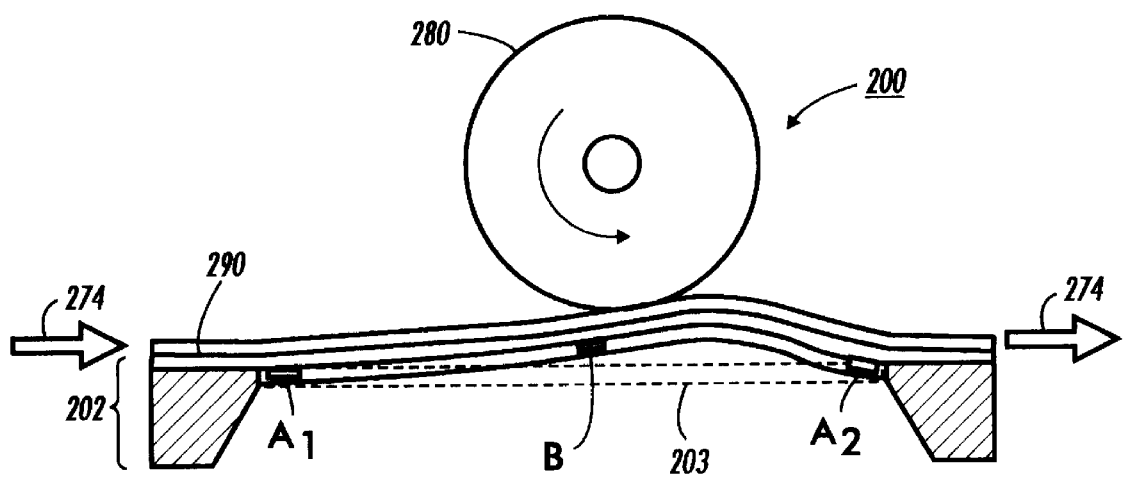
FIG. 11 is a cross-sectional view of a first embodiment of the paper property sensor system of the present invention.
Figure 12:
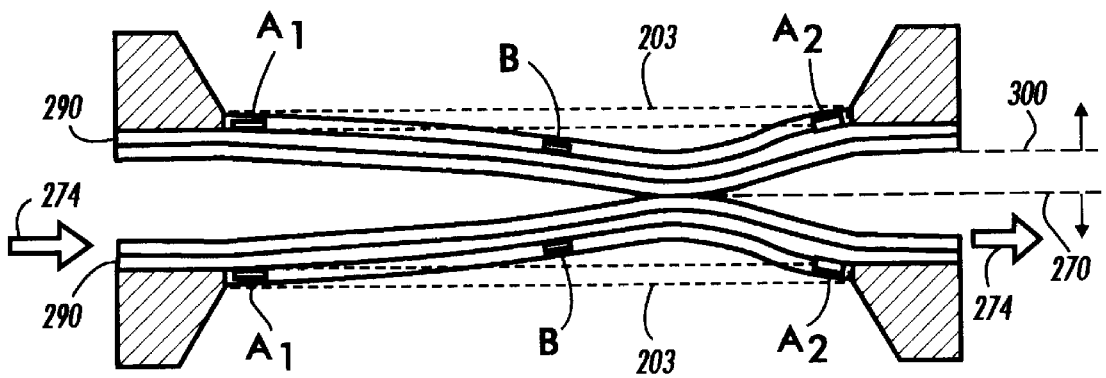
FIG. 12 is a cross-sectional view a second embodiment of the paper property sensor system of the present invention.

FIG. 11 illustrates in cross section one embodiment of paper property sensor system 200. Roller 280 opposes surface 270 and its tactile arrays 202. Arrows 274 indicate the direction of sheet 272 through nip 200. Skin 290 protects diaphragm 202 from abrasion and distributes forces uniformly over tactile array 202. FIG. 12 illustrates in cross section another embodiment of paper property sensor system 200, two surfaces 270 and 300 opposed to each other. Each surface includes tactile arrays in opposition to those of the other surface.

D. Conclusion

Thus, a paper property sensor system has been described that includes a surface and a diaphragm opposed to each other. The small diaphragm includes a first pair and a second pair piezoresistors. Each piezoresistor of the first pair is located perpendicular to and very close to one of the long edges of the diaphragm. Each piezoresistor of the second pair is located between and parallel to first pair of piezoresistors, and away from the short edges of the diaphragm. Balancing the first pair of piezoresistors against the second pair in a Wheatstone bridge, produces a voltage dependent on the thickness of a sheet. Balancing the resistors of the first pair against each other, and the resistors of the second pair against each other generates a voltage dependent on the coefficient of friction of the sheet.

In the foregoing specification, the invention has been described with reference to specific exemplary embodiments thereof. It will, however, be evident that various modifications and changes may be made thereto without departing from the broader spirit and scope of the invention as set forth in the appended claims. Accordingly, the specification and drawings are to be regarded in an illustrative rather than a restrictive sense.

What is claimed is:

1. A sensor system for measuring a shear force exerted by a sheet of material, the sensor system comprising:

a) a surface in contact with the sheet of material; and b) a first diaphragm located opposite the surface and in contact with the sheet of material, the diaphragm being rectangular and having a pair of short edges and a pair of longer edges, the longer edges being less than 2 cm in length, the short edges having a first length, the diaphragm including a first pair of piezoresistors and second pair of piezoresistors, each piezoresistor of the first pair having a longitudinal axis being located adjacent and perpendicular to a one of the longer edges, each piezoresistor of the second pair having a longitudinal axis being located between the first pair of piezoresistors and perpendicular to a one of the longer edges, each piezoresistor of the second pair being located at least a half of the first length away from each of the short edges;

the first pair and the second pair of piezoresistors being coupled together electrically to produce a first electrical signal representative of the shear force exerted by the sheet of material.

2. The sensor system of claim 1 wherein the first diaphragm comprises a semiconductor material.

3. The sensor system of claim 2 wherein the first diaphragm is made of silicon.

4. The sensor system of claim 2 wherein the first and second pair of piezoresistors are fabricated by diffusion.

5. The sensor system of claim 1 wherein the first pair and the second pair of piezoresistors are coupled together electrically to produce a second electrical signal representative of a normal force exerted by the sheet of material.

6. The sensor system of claim 5 wherein the diaphragm includes another pair of the first pair of piezoresistors and another pair of the second pair of piezoresistors.

7. The sensor system of claim 1 wherein the surface comprises a roller.

8. The sensor system of claim 1 wherein the surface comprises a second diaphragm, the second diaphragm being identical to the first diaphragm.

9. The sensor system of claim 5 wherein a one of the first pair and a one of the second pair of piezoresistors are located to experience a force exerted by the sheet of material and an other of the first pair and an other of the second pair of piezoresistors are located to not experience the force exerted by the sheet of material.

10. The sensor system of claim 5 wherein the normal force exerted by the sheet of material is used to determine a thickness of the sheet of material.

11. The sensor system of claim 10 wherein the the shear and normal forces exerted by the sheet of material are used to determine a coefficient of friction of the sheet of material.

12. The sensor system of claim 1 wherein the sheet of material comprises a sheet of paper.

13. The sensor system of claim 1 wherein the sheet of material comprises a transparency.

14. The sensor system of claim 1 wherein the first and second pair of piezoresistors are coupled together to form a Wheatstone Bridge.

15. A nip for sensing a coefficient of friction of a sheet of material, the nip comprising:

a) a roller in contact with the sheet of material; and b) a semiconductor diaphragm located opposite the surface and in contact with the sheet of material, the semiconductor diaphragm being rectangular and having a pair of short edges and a pair of longer edges and a depth, the longer edges being less than 2 cm in length, the short edges having a first length, the depth being substantially less than the first length, the semiconductor diaphragm including a first pair of piezoresistors and second pair of piezoresistors, each piezoresistor of the first pair being located adjacent and perpendicular to a one of the longer edges, each piezoresistor of the second pair being located between the first pair of piezoresistors and perpendicular to a one of the longer edges, each piezoresistor of the second pair being located at least a half of the first length away from each of the short edges;

the first pair and the second pair of piezoresistors being coupled together electrically to produce a first electrical signal representative of a shear force exerted by the sheet of material and a second electrical signal representative of a normal force exerted by the sheet of material, a ratio of the shear force to the normal force being representative of the coefficient of friction of the sheet of material.

16. The nip of claim 15 wherein the first and second pair of piezoresistors are coupled together to form a Wheatstone Bridge.

17. The nip of claim 16 wherein the normal force represents a thickness of the sheet of material.

18. The nip of claim 14 wherein the semiconductor diaphragm comprises a silicon diaphragm.

19. The nip of claim 14 wherein the semiconductor diaphragm includes a multiplicity of first pairs of piezoresistors and of second pairs of piezoresistors.

20. The nip of claim 19 wherein some of the multiplicity of first and second pairs of piezoresistors are located to experience a force exerted by the sheet of material and others of the multiplicity of first and second pairs of piezoresistors are located to not experience the force exerted by the sheet of material.

21. A nip for sensing the thickness and the coefficient of friction of a sheet, the nip comprising:

a pair of semiconductor diaphragms opposed to each other and located to experience a force exerted by the sheet, each of the pair semiconductor diaphragms being rectangular and having a pair of short edges and a pair of longer edges and a depth, the longer edges being less than 2 cm in length, the short edges having a first length, the depth being substantially less than the first length, each of the pair of semiconductor diaphragms including a first pair of piezoresistors and second pair of piezoresistors, each piezoresistor of the first pair being located adjacent and perpendicular to a one of the longer edges, each piezoresistor of the second pair being located between the first pair of piezoresistors and perpendicular to a one of the longer edges, each piezoresistor of the second pair being located at least a half of the first length away from each of the short edges;

the first pair and the second pair of piezoresistors being coupled together electrically to form a first Wheatstone bridge to produce a first electrical signal representative of the thickness and being coupled together electrically to form a second Wheatstone bridge to produce a second electrical signal representative of the coefficient of friction.

22. The nip of claim 21 wherein each of the pair of semiconductor diaphragms comprises a silicon diaphragm.

23. The nip of claim 22 wherein each of the pair of semiconductor diaphragms includes a multiplicity of first pairs of piezoresistors and of second pairs of piezoresistors.

* * * * *